United States Patent

Sabins

[11] 4,107,017
[45] Aug. 15, 1978

[54] ANODE ANALYZER

[75] Inventor: Todd C. Sabins, El Cajon, Calif.

[73] Assignee: Sabins Industries, Inc., Long Beach, Calif.

[21] Appl. No.: 740,116

[22] Filed: Nov. 8, 1976

[51] Int. Cl.² .................. G01N 27/46; C23F 13/00
[52] U.S. Cl. ........................ 204/195 R; 204/195 F; 204/148; 204/197; 324/115
[58] Field of Search ........... 204/195 R, 195 F, 147, 204/148, 196, 197; 324/115, 116

[56] References Cited

U.S. PATENT DOCUMENTS

| | | | |
|---|---|---|---|
| 2,183,531 | 12/1939 | Allison | 204/195 F |
| 2,792,549 | 5/1957 | Bernreuter | 324/115 |
| 3,117,070 | 1/1964 | Anderson | 204/195 F |
| 3,192,144 | 6/1965 | Heuze | 204/195 F |
| 3,360,452 | 12/1967 | McNulty | 204/197 |
| 3,365,663 | 1/1968 | Yamaguchi | 324/115 |
| 3,591,481 | 7/1971 | Riseman | 204/195 R |
| 3,806,797 | 4/1974 | Harvey | 324/115 |
| 3,941,665 | 3/1976 | Elkfeldt et al. | 204/195 R |

Primary Examiner—T. Tung
Attorney, Agent, or Firm—Trask & Britt

[57] ABSTRACT

An electrical system for measuring the relative level of protection afforded a structure against corrosion caused by electrochemical reaction where such structure is so protected by a system of sacrifical anodes. This instrument is constructed with a magnesium alloy anode and calibrated to read with reference to any of the three standard voltage reference half cells currently used in the industry, specifically copper-copper sulfate, silver-silver chloride, and saturated calomel.

10 Claims, 2 Drawing Figures

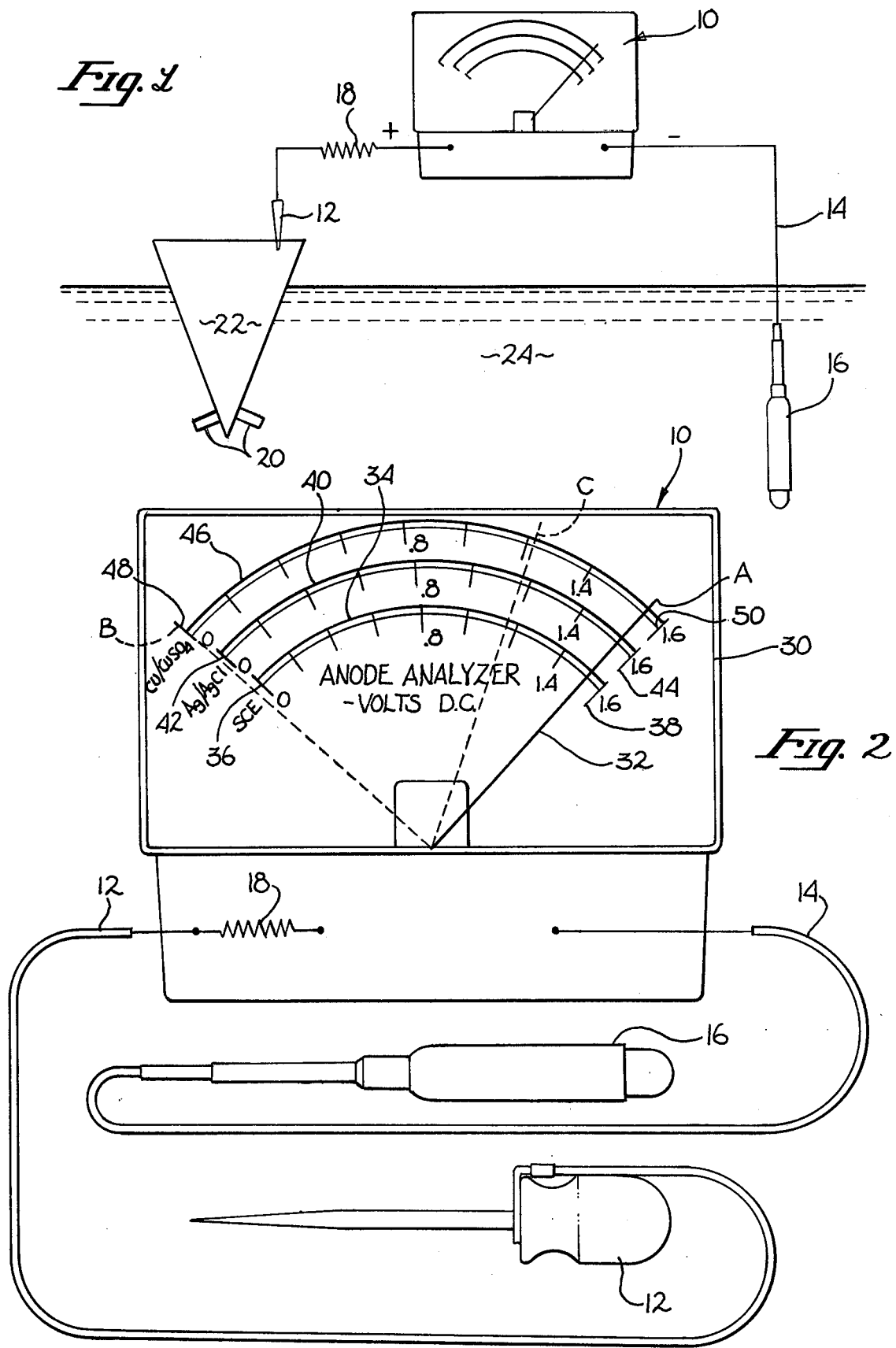

ANODE ANALYZER

BACKGROUND OF THE INVENTION

1. Field of the Invention

This invention relates to the field of electrical systems and meters designed to measure electrical potential difference and more specifically to instruments designed to interpret potential difference as a relative measure of the effectiveness of sacrifical anodes in protecting structures from corrosion, such structures typically being ships in salt water.

2. Prior Art

In order to protect the hull of a ship from electrochemical corrosion, it is common practice to attach to the hull of the ship a material which has an electrochemical reaction potential more negative than that of the material of which the hull is constructed. In this manner, the material attached to the hull will give off electrons more readily than the hull thereby protecting the hull from corrosion. Such systems are commonly referred to as sacrificial cathodic protection systems. When the sacrificial material is corroded to an extent that it can no longer effectively protect the hull from corrosion, the material is replaced.

The present invention is utilized to detect the point at which the sacrificial anodes should be replaced. This instrument, however, is not limited to use in conjunction with ships.

Corrosion engineers typically use one of the three standard half cell reference voltages when measuring potential difference in corrosion systems. For land-based structures protected by sacrificial anodes, the standard reference is the copper-copper sulfate half cell. For the scientific experimental or laboratory situation, the reference voltage is that of a saturated calomel half cell (calomel is mercurous chloride). The silver-silver chloride cell is the standard reference half cell used for corrosion measurements relating to sea-based installations (such as ships).

Because of the chronology of historical development, all of the prior art instruments have been constructed specifically for use in one of the above three environments. An instrument designed for use in one environment could not conveniently be used in another environment. It is therefore an object of the present invention to provide an instrument which can be used to measure the relative effectiveness of sacrificial cathodic systems as conveniently in one environment as in either of the others.

All electrical instruments designed to measure potential difference have two terminals. In prior art instruments designed to evaluate the relative effectiveness of a sacrificial anode system, one terminal is attached to one of the three standard reference half cells. In these prior art devices, the reference half cells always had a more positive electrochemical reaction potential than the hull of a ship. Thus the flow of electrons in such devices would be from the hull of the ship through the instrument to the reference half cell. Due to the small surface area of the reference half cell, it would become polarized quite quickly to a level which would interfere with accurate measurements.

The device of the present invention uses as its reference half cell a probe of magnesium alloy AZ63 (magnesium, 6% aluminum, 3% zinc, 0.2% manganese and traces of impurities), which has an electrochemical reaction potential which is more negative than that of the hull, thereby causing the electrons to flow from the half cell through the meter to the hull of the ship. The number of electrons which in the prior art devices would flow to the reference half cell, and polarize it such that accurate measurements could not be made, are now caused to flow to the ship where they are distributed over its much larger surface area. The effect of the electrons on such a large surface area is negligible and does not interfere with the accuracy of readings. This allows readings to be taken for much longer time periods without loss of accuracy as compared with prior art devices.

The other terminal of the present invention is used for making the electrical connection between the meter and the structure being tested, for example the hull of a ship. In the present invention, this terminal terminates in a body of metal having a sharp point and generally shaped like an ice pick so that the body of metal is more readily forced through any layers of paint or of barnacles which may be adhering to the hull and make a good electrical connection with the hull.

The prior art devices used half cells of silver-silver chloride, copper-copper sulfate and calomel (mercurous chloride). Each of those half cells has a brittle exterior layer which is easily shattered upon impact. The half cell used in the present invention is a homogeneous alloy of magnesium, having no brittle exterior layer.

The magnesium alloy also acts as an anode and thus will repel any slight coating of oil which it may receive when immersed in the water of a typical harbor. The devices of the prior art have an electron flow in the opposite direction and will not repel these coatings of oil, which tend to interfere with the accuracy of measurements.

The magnesium alloy half cell may also be cleaned as required by a wire brush similar to that used to clean battery terminals.

These and other objects and advantages of the present invention will become apparent as the description is read in conjunction with the drawings.

SUMMARY OF THE INVENTION

The system of the present invention comprises a voltmeter having a full scale sensitivity of 1.6 V.D.C. and a 20,000 ohms per volt movement. The meter is assembled with the indicator needle movement rotated clockwise so that the needle rests at the right hand end of the scales when non-energized. When the negative terminal of the meter is connected to a negative source of current and the positive terminal connected to the positive terminal of the current source, the needle is deflected from right to left across the scales a distance proportional to the voltage of the source of current.

The indicating scales provide left hand zeroes, indicating increasing potential from left to right, thereby providing an instrument which indicates a back electromotive force. This indicates the magnitude of any voltage opposing the potential of electrochemical reaction of the negative terminal preferably made of AZ63 magnesium alloy. Because the magnesium alloy has an electrochemical reaction potential more negative than any anode used to protect the hull of a ship or other structure, the magnesium alloy will not become polarized during the taking of a reading, and in actuality is a self-cleaning probe. The magnesium half cell probe thereby permits longer readings to be taken without loss of accuracy.

The present invention thus provides a system for measuring electrical potential comprised of a voltmeter whose indicator needle is at full scale when non-energized and deflects toward the zero or left hand end when energized. One terminal of the meter is permanently affixed to a mass of magnesium alloy AZ63 of generally cylindrical shape having a diameter of about ⅝ inch and a length of about 4½" and a weight on the order of 1½ ounces. The meter has three scales offset with respect to one another, so that the potential detected by the meter can be read with respect to the standard half cell reference desired, either copper-copper sulfate, silver-silver chloride or saturated calomel.

DESCRIPTION OF THE DRAWINGS

FIG. 1 is a schematic illustration showing the use of the device of the present invention.

FIG. 2 is a detail view of the three calibrated scales placed on the face of the meter used in the system of the present invention.

DESCRIPTION OF THE PREFERRED EMBODIMENT

The system of the present invention illustrated in FIG. 1 comprises a voltmeter 10 having a positive terminal 12 and a negative terminal 14. Permanently affixed to the negative terminal is a probe 16 of magnesium alloy commonly known as AZ63. This probe is a reference half cell. The voltmeter has a movement of 20,000 ohms per volt, represented by resistor 18. This system is used to measure the relative effectiveness of sacrificial anodes 20 in protecting, from electrochemical corrosion, a structure 22, which is located within an electrolytic medium 24.

By way of example, the electrolytic medium 24 may be sea water. The structure 22 may be an ocean-going cargo vessel in which case the hull of the ship is likely an alloy of steel. It has been common practice to protect the steel hulls of ships by cathodic protection. This protection is achieved by placing anodes 20, of a material having a more negative potential of electrochemical reaction than the material of which the hull of the ship 22 is made, at intervals along the length of the hull. These anodes are normally insulated from direct metallic contact with the hull; the electrical circuit is completed through the fastening bolts (not shown), set in countersunk holes in the anode 20 (which is commonly zinc), or zinc cast on metal straps welded to the hull.

Since the steel hull of the ship 22 and the zinc anodes 20 constitute two dissimilar metals immersed in an electrolytic medium 24, an electrochemical reaction takes place and the anode 20, which has a more negative potential of electrochemical reaction, corrodes more readily than the hull, thereby protecting the steel hull of the ship 22 from corrosion. This electrochemical reaction produces a potential difference between the hull of the ship 22 and the electrolytic medium 24. This potential will be referred to at various times herein as the back E.M.F. As the electrochemical reaction progresses, the anodes 20 corrode and lose their effectiveness, accordingly the electrochemical potential between the hull of the ship 22 and the electrolytic medium 24 decreases. When the back E.M.F. falls below a predetermined level this indicates that the anodes 20 have lost their effectiveness and should be replaced.

To understand the manner in which the system of the present invention indicates the back E.M.F., it is necessary to first examine the structure of the meter 10, more fully illustrated in FIG. 2.

Meter 10 has a body 30 and an indicator needle 32, as well as terminals 12 and 14 and internal resistance 18 previously identified. Needle 32 when non-energized is positionally rotated so as to rest in position A. If the needle should become fully energized it would assume the full deflection position indicated in phantom at position B. If the sacrificial anode system of a ship is new and properly functioning and designed to keep the hull 22 at a potential of −1.0 volt relative to that of the electrolyte, with reference to a silver-silver chloride half cell reference, the meter 10 will indicate 1 volt on the silver-silver chloride scale 40 as indicated at C. It should be noted that the meter of FIG. 2 reads negative volts. The meter simultaneously shows the potential of the hull with respect to the three standard reference half cells on three scales.

The first scale is referred to as the saturated calomel reference scale 34. This scale has a non-energized needle position of 38 and a full deflection point at 36. The non-energized position has a numerical scale indication of about −1.58v and a full deflection numerical reading of about +0.01v. This is the reference scale normally used in a laboratory setting.

The second scale is the silver-silver chloride reference scale 40. This scale has a non-energized needle position of 44 and a full deflection point at 42. The non-energized position has a numerical scale indication of about −1.59v but is calibrated to −1.60v and has a full deflection reading of 0.00v. This is the reference scale normally used when making corrosion readings in a marine environment.

The third scale is the copper-copper sulfate reference scale 46. This scale has a non-energized needle position of 50 and a full deflection point at 48. The non-energized position has a numerical scale indication of about −1.64v and a full deflection reading of about −0.05v. This is the reference scale normally used when making corrosion readings on a land based structure such as a pipeline embedded in the ground.

The operation of the preferred embodiment as illustrated in FIG. 1 may be described in the following manner. The assumption is made that the ship to be protected is equipped with a sacrificial anode cathodic system which maintains the potential of the ship at −1000mv with respect to a silver-silver chloride reference half cell.

The positive terminal of the meter is placed in electrical contact with the hull of the ship, while the magnesium alloy AZ63 which is attached to the negative terminal of the meter is immersed in the same electrolytic solution as the hull of the ship.

When so immersed the magnesium alloy has an electrochemical reaction potential of −1.59v with respect to a silver-silver chloride reference half cell. The non-energized needle will therefore come to rest over the number 1.59 on the silver-silver chloride scale 40. The steel hull is sacrificially controlled to be at −1.000v with respect to the same reference. Therefore the voltmeter 10 will detect the difference in voltage levels, or −0.59 volts. This −0.59 volts will cause a deflection of the needle 32 a distance to the left proportional to −0.59 volts. Since full scale on scale 40 is −1.60 volts, and the non-energized needle 32 is at rest at −1.59 volts, and the scale readings increases from left to right, the needle will come to rest over the number 1.0 on the scale 40, indicating negative one volt. This is calculated as −1.59 volts non-energized needle position minus −0.59 volts sensed, equals −1.0 volts on the scale. A reading of 1.0 on scale 40 indicates that the anodes are fully effective and operating as designed, maintaining the hull at −1.00 volts.

After the sacrificial anode system has been operating for a few years, the anodes 20 will have deteriorated to some extent, and possibly even to the extent that the control system cannot maintain the ship at −1.000v. Suppose the best that can be maintained is a ship hull potential of −0.8v. The meter 10 will now detect the difference between the −1.59v. of the magnesium alloy and the −0.8 volts of the ship hull, or −0.79v. This voltage is detected by the meter causing a deflection of the needle to the left a distance proportional to −0.79 volts. This will produce a reading on scale 40 of −(1.59 − 0.79) or −0.8 volts. It can thus be seen that the reading on scale 40 corresponds to the potential level of the hull of the ship, i.e. back E.M.F.

After a while the anodes 20 will deteriorate and corrode to the point where they can not maintain a ship hull potential below −0.580 volts. The meter 10 will thus detect the difference in potential, between the magnesium and the hull, of −1.59v minus −0.580 or −1.01 volts. The needle will deflect to the left a distance proportional to −1.01 volts and will therefore come to rest at a reading on the scale 40 of −1.59 minus −1.01 or −0.580 volts. This reading is above the acceptable industry absolute minimum of −0.585 volts and indicates that the anodes should be replaced if excessive corrosion of the hull is to be avoided.

The operation of the system is very similar when measuring the effectiveness of anodes protecting structures embedded in land. For example, structure 22 could be a metal pipe, having zinc protective anodes. To measure the effectiveness of the anodes, the positive terminal of the meter is brought into electrical contact with the pipe. The magnesium probe is embedded in the land adjacent to the pipe and soaked with water to insure good electrical conduction. As long as the magnesium has a more negative electrochemical reaction potential than that of the structure being tested for corrosion, the meter will detect the potential difference between the structure and magnesium and the needle will deflect to the left a distance proportional to the voltage difference.

Suppose that the electrochemical reaction potential of the magnesium in a soil electrolyte, with reference to a copper-copper sulfate standard reference half cell, is −1.64 volts. The non-energized position of the needle then reads −1.64 volts on the copper-copper sulfate scale 46. If the cathodic protection had been designed to keep the pipe at a potential of −0.8 volts above the copper-copper sulfate reference cell then the meter will detect the difference of −1.64 minus −0.8 or −0.084 volts. The needle would then defelct to the left a distance proportional to −0.84 volts and come to rest at −1.64 minus −0.84 or −0.8 volts on the copper-copper sulfate scale.

As the anodes corrode, the potential of the pipe rises, the potential difference between the magnesium and pipe therefore increases, resulting in greater leftward deflection of the needle and a corresponding smaller reading on the copper-copper sulfate scale.

The system can similarly be used for taking corrosion readings in the laboratory with respect to a saturated calomel standard reference half cell.

It will be noted that the electrochemical reaction potential of the magnesium was assumed to remain at a fixed level. This is so because the magnesium has a more negative electrochemical reaction potential than the material being tested and therefore as between the tested material (which has a large surface area) and the magnesium alloy the tested material (or its protective anodes) will tend to polarize during the test and not the magnesium alloy. The magnesium alloy is the element from which electrons travel through the meter to the structure being tested, it therefore will not become polarized. The magnesium alloy probe therefore maintains its accuracy for longer periods than devices of the prior art and also maintains accuracy even if it is immersed into oily water and is thus coated with oil during a test. The flow of electrons from the magnesium alloy through the meter to the strucutre tends to keep the magnesium alloy free of coatings of corrosion and debris.

While the invention has been particularly shown and described with reference to a preferred embodiment thereof, it will be understood by those skilled in the art that various changes in form and details therein may be made without departing from the spirit and scope of the invention.

What is claimed is:

1. An apparatus for evaluating the effectiveness of anodes in a cathodic protection system protecting a structure in an electrolyte from electrochemical corrosion, said apparatus comprising:

a voltmeter having a positive terminal and a negative terminal, said negative terminal being conductively connected to a reference half cell member and said positive terminal being conductively connected to said structure;

said reference half cell which is a probe immersed in said electrolyte and which is made of an alloy of magnesium known as AZ 63 which has an electrochemical reaction potential more negative than the structure protected by said cathodic protection system when positioned in said electrolyte;

said voltmeter having a plurality of scales thereon, and an indicator needle moveable across the plurality of scales in response to a potential difference appearing between said positive and negative terminals;

each of said plurality of scales having a sequence of numbers placed therealong and each scale being so placed beneath the indicator needle that when the indicator needle comes to rest the number beneath the indicator needle indicates the negative of the electrochemical potential of the structure with respect to the voltage of a standard reference half cell for which that scale is calibrated.

2. An apparatus for evaluating the effectiveness of anodes in a cathodic protection system protecting a structure from electrochemical corrosion in an electrolyte, said apparatus comprising:

a voltmeter having a positive terminal and a negative terminal, said negative terminal being conductively connected to a reference half cell made of the magnesium alloy commonly known as AZ63 positioned in said electrolyte, and said positive terminal being conductively connected to said structure;

said voltmeter having three scales upon each of which is placed an ordered sequence of numbers such that the potential difference appearing between said positive and negative terminals may be read thereon;

the first scale being calibrated to indicate a potential difference with reference to a standard saturated calomel half cell;

the second scale being calibrated to indicate a potential difference with reference to a standard silver-silver chloride half cell;

the third scale being calibrated to indicate a potential difference with reference to a standard copper-copper sulfate half cell;

an indicator needle moveable across the three scales in response to a potential difference between said positive and negative terminals and said indicator needle being oriented such that in its non-energized state it rests over those ends of the scales which are labeled with the highest numbers in the sequence.

3. The apparatus of claim 2 wherein the indicator needle, in response to an increasing potential difference between the positive and negative terminals, moves across the scales from the higher numbers of a sequence toward the lower numbers of the sequence.

4. The apparatus of claim 3 wherein the full scale deflection of the indicator needle represents a potential difference between the positive and negative terminals of ⊖1.590 volts and results in the needle coming to rest over that end which is labeled zero volts on that scale which is referenced to a silver-silver chloride standard half cell.

5. The apparatus of claim 4 wherein the left hand end of each scale is labeled zero volts.

6. An apparatus comprising a voltmeter and probe, said voltmeter having a positive terminal and a negative terminal, useful for measuring the electrochemical reaction potential of a structure immersed in an electrolyte wherein said positive terminal is brought into electrical contact with the structure and the negative terminal is securely and electrically directly attached to said probe which is a reference half cell made of an alloy of magnesium commonly known as AZ63, which half cell is also immersed in said electrolyte thereby causing electrons to flow from said half cell through said meter to said structure during the time the electrochemical reaction potential of said structure is being measured, thereby causing the polarization of said structure rather than said half cell of said apparatus during such time.

7. The apparatus of claim 6 wherein the voltmeter has three scales upon which the potential difference appearing between the first and second terminals may be simultaneously read with respect to different standards, each scale indicating the potential difference with reference to a different one of the standard half cells of copper-copper sulfate, silver-silver chloride or saturated calomel construction. of the standard half cells of copper-copper sulfate, silver-silver chloride or saturated calomel construction.

8. The apparatus of claim 7 wherein the voltmeter has an indicator needle which, in its non-energized position, is at rest over the end of the scales labeled with the highest numbers and which, in its fully energized position, is at rest over the end of the scales labeled with the lowest numbers.

9. Apparatus for measuring the potential between a cathodic structure in an electrolytic medium and said medium, said apparatus comprising:

a meter having a positive terminal, a negative terminal and indication means;

first connection means which electrically connects said positive terminal to a cathodic structure in an electrolytic medium;

a probe positioned in said medium and made of an alloy of magnesium known as AZ 63 electrochemically more negative than the material of said cathodic structure;

second connection means which electrically connects said probe to said negative terminal;

wherein said cathodic structure acts as a cathode and said probe is an anode with electron flow from said probe to said cathodic structure through said meter which is calibrated with respect to a standard so that said indication means indicates the electric potential between said cathodic structure and said medium.

10. The apparatus of claim 9 wherein said indication means of said meter has three scales and wherein said meter is calibrated to simultaneously indicate the electric potential between said cathodic structure and said medium on each scale, a first scale of said three scales indicating said potential with reference to a standard saturated calomel half cell, a second of said three scales indicating said potential with reference to a standard silver-silver chloride cell, and a third of said three scales indicating said potential with reference to a standard copper-copper sulfate cell.

* * * * *